(12) United States Patent
Melnick et al.

(10) Patent No.: US 9,072,604 B1
(45) Date of Patent: Jul. 7, 2015

(54) MODULAR TRANSCATHETER HEART VALVE AND IMPLANTATION METHOD

(71) Applicants: Gilberto Melnick, Curitiba (BR); Enio Eduardo Guerios, Curitiba (BR)

(72) Inventors: Gilberto Melnick, Curitiba (BR); Enio Eduardo Guerios, Curitiba (BR)

(*) Notice: Subject to any disclaimer, the term of this patent is extended or adjusted under 35 U.S.C. 154(b) by 0 days.

(21) Appl. No.: 14/563,933

(22) Filed: Dec. 8, 2014

Related U.S. Application Data (60) Provisional application No. 61/938,620, filed on Feb. 11, 2014.

(51) Int. Cl.
*A61F 2/24* (2006.01)

(52) U.S. Cl.
CPC .............. *A61F 2/2418* (2013.01); *A61F 2/2433* (2013.01); *A61F 2210/0014* (2013.01)

(58) Field of Classification Search
USPC ........... 623/1.26, 2.11, 2.12, 2.13, 2.14, 2.15, 623/2.16, 2.18, 2.19, 2.36, 2.37
See application file for complete search history.

(56) References Cited

U.S. PATENT DOCUMENTS

| | | | |
|---|---|---|---|
| 5,411,552 A | 5/1995 | Andersen et al. | |
| 6,425,916 B1 * | 7/2002 | Garrison et al. | 623/2.11 |
| 6,908,481 B2 * | 6/2005 | Cribier | 623/2.11 |
| 8,002,826 B2 | 8/2011 | Seguin | |
| 2005/0137691 A1 | 6/2005 | Salahieh et al. | |
| 2006/0271166 A1 | 11/2006 | Thill et al. | |
| 2006/0287719 A1 | 12/2006 | Rowe et al. | |
| 2007/0203503 A1 * | 8/2007 | Salahieh et al. | 606/108 |
| 2008/0077234 A1 * | 3/2008 | Styrc | 623/2.11 |
| 2009/0319037 A1 | 12/2009 | Rowe et al. | |
| 2012/0143301 A1 | 6/2012 | Maslanka et al. | |
| 2012/0271411 A1 | 10/2012 | Duhay et al. | |

FOREIGN PATENT DOCUMENTS

| | | |
|---|---|---|
| WO | WO 2010/086460 | 8/2010 |
| WO | WO 2010/117609 | 10/2010 |
| WO | WO 2012/177942 | 12/2012 |
| WO | WO 2013/114214 | 8/2013 |

* cited by examiner

*Primary Examiner* — Tuan V Nguyen
(74) *Attorney, Agent, or Firm* — Knobbe, Martens, Olson & Bear, LLP (57) ABSTRACT

Disclosed herein are valves, such as an aortic valve replacement can be delivered via a transcatheter approach can be deployed by a single operator through a lower profile (e.g., 8-12 French, or even less) delivery system. Lower profile delivery systems can advantageously potentially expedite procedures and reduce complications, as they tend to be easier to navigate through the vascular anatomy. In some embodiments, the valve system can be deployed in a multiple stage approach as two separate components, rather than a single unified component; first a stent, followed by a discrete structure such as a valve support that includes the valve leaflets. The components can be positioned separately during delivery at different locations in and over the catheter. The stent can include a pair of rows of hooks directed in directions opposite to one another. The valve support can include struts having retaining structures that form a spherical configuration when retained together by a grasping member to keep the valve folded and conical during delivery thereof inside the catheter.

21 Claims, 10 Drawing Sheets

MODULAR TRANSCATHETER HEART VALVE AND IMPLANTATION METHOD

REFERENCE TO RELATED APPLICATIONS

This application claims the benefit under 35 U.S.C. §119 (e) as a nonprovisional of U.S. Pat. App. No. 61/938,620 filed on Feb. 11, 2014, which is hereby incorporated by reference in its entirety.

BACKGROUND

The invention relates to, in some aspects, heart valves and methods of using the same.

SUMMARY

In some embodiments, disclosed herein is a heart valve replacement system. The system can include a delivery catheter having a proximal end, a central lumen, and a distal end. The system can also include a scaffold stent configured to fit over a portion of the delivery catheter proximate the distal end of the delivery catheter. The scaffold stent can have a reduced delivery configuration and an expanded configuration. The system can also include a valve support comprising a frame and a plurality of leaflets attached to the frame. The frame can include a plurality of struts, such as 2, 3, or more struts extending axially from the frame. Each strut can have a retaining structure at its downstream end. The valve support can have a reduced delivery configuration where the valve support can be housed within the central lumen of the delivery catheter. The valve support can be configured to be delivered independent of the scaffold stent. The system can also include a grasping member, such as a bioptome or snare for example, configured to operably attach to the retaining structures of the struts to compress the valve leaflets. The system can also include an expandable member, e.g., a balloon, proximate the distal end of the delivery catheter, the expandable member configured to expand the scaffold stent. The scaffold stent can also be self-expandable, and a retractable sheath or other retaining mechanism can be configured to maintain the scaffold stent in a reduced configuration during delivery. The retaining structures of the struts can be releasably attached to the grasping member, and the retaining structures can couple together to form a sphere-like shape. The delivery catheter can have a size of less than or equal to 12 French, such as between 8 French and 12 French. The frame of the valve support can be made of a shape memory mesh material. The valve skirt can be attached to an inner or outer surface of the scaffold stent, and can be made of, for example, a fabric material. The frame of the valve support can include a generally cylindrical portion, and a flap portion on an upstream end of the frame configured to rest against an upstream end of the scaffold stent. The flap portion can be configured to minimize or prevent paravalvular regurgitation. The system can be configured to replace a native aortic, mitral, tricuspid, or pulmonic valve.

Also disclosed herein is a transluminal method of delivering a heart valve replacement, such as an aortic valve replacement. The method can include one or more of the steps of providing a delivery catheter carrying a scaffold stent over a distal portion of the delivery catheter, the scaffold stent having an upstream end and a downstream end, the delivery catheter also comprising a valve support having a frame, a plurality of valve leaflets, and a distal flap portion, the valve support carrying a prosthetic aortic valve releasably connected to a delivery cable, the valve support not connected to the scaffold stent. The method can also include positioning the distal end of the delivery catheter in the left ventricle, to position the scaffold stent at the level of the native aortic valve annulus. The method can further include expanding the scaffold stent within the native aortic valve annulus; partially moving the valve support out of the delivery catheter, thereby expanding, the distal flap portion; retracting the valve support such that the distal flap contacts the upstream end of the scaffold stent; disconnecting the valve from the delivery cable; and withdrawing the delivery catheter and the delivery cable. Disconnecting the valve from the delivery cable can include releasing a grasping member, e.g., a bioptome or snare for example, connected to retaining structures on proximal ends of struts extending from the valve support, whereby release of the bioptome causes the valve leaflets to completely unfold. The method can also include securing the valve support to the scaffold stent. Securing the valve support to the scaffold stent can include connecting the frame of the valve support to hooks on a radial inwardly-facing surface of the scaffold stent. Expanding the scaffold stent within the native aortic valve annulus can include balloon-expanding the scaffold stent, or allowing the scaffold stent to self-expand.

DETAILED DESCRIPTION

Heart valve replacement has become a routine surgical procedure for patients suffering from valve regurgitation or stenotic calcification of the leaflets. While certain procedures may be performed using minimally-invasive or transluminal techniques, the vast majority of valve replacements still entail full sternotomy and placing the patient on cardiopulmonary bypass. Traditional open surgery inflicts significant patient trauma and discomfort, requires extensive recuperation times and may result in life-threatening complications.

More recently, efforts have been focused on percutaneous transluminal delivery of replacement cardiac valves to solve the problems presented by traditional open surgery and minimally-invasive surgical methods. In such methods, a valve prosthesis is compacted for delivery in a catheter and then advanced, for example, through an opening in the femoral artery and through the descending aorta to the heart, where the prosthesis then is deployed over the aortic valve annulus. Although transluminal techniques have attained widespread acceptance with respect to delivery of stents to restore vessel patency, only mixed results have been obtained with respect to percutaneous delivery of relatively more complicated valve prostheses. Stent-supported systems for positioning of a replacement heart valve could potentially have issues with regard to migration from the target valve site, and vascular complications due to the relatively high profile of the valve system. What is needed are replacement valves that are less prone to migration, and furthermore can be delivered safely and efficiently via a low-profile delivery system.

The deployment of a transcatheter valve, such as an aortic or mitral valve for example, as a whole unit can require relatively large-diameter catheters or delivery systems. Disclosed herein are valves, such as an aortic valve replacement that can be delivered via a transcatheter approach and can be deployed by a single operator through a lower profile (e.g., 8-12 French, or even less) delivery system. Lower profile delivery systems can advantageously potentially expedite procedures and reduce complications, as they tend to be easier to navigate through the vascular anatomy. In some embodiments, the valve system can be deployed in a multiple stage approach as two separate components, rather than a single unified component; first a scaffold stent, followed by a discrete structure such as a valve support that includes the valve leaflets. The components can be positioned separately during delivery at different locations in and over the catheter. The stent can include a pair of rows of hooks disposed in a parallel or substantially parallel manner or directed in directions opposite to one another. The valve support can include struts having retaining structures that form a spherical configuration when retained together by a grasping member to keep the valve leaflets folded and conical during delivery thereof inside the catheter, advantageously creating a significantly reduced delivery profile.

Figure 1A:
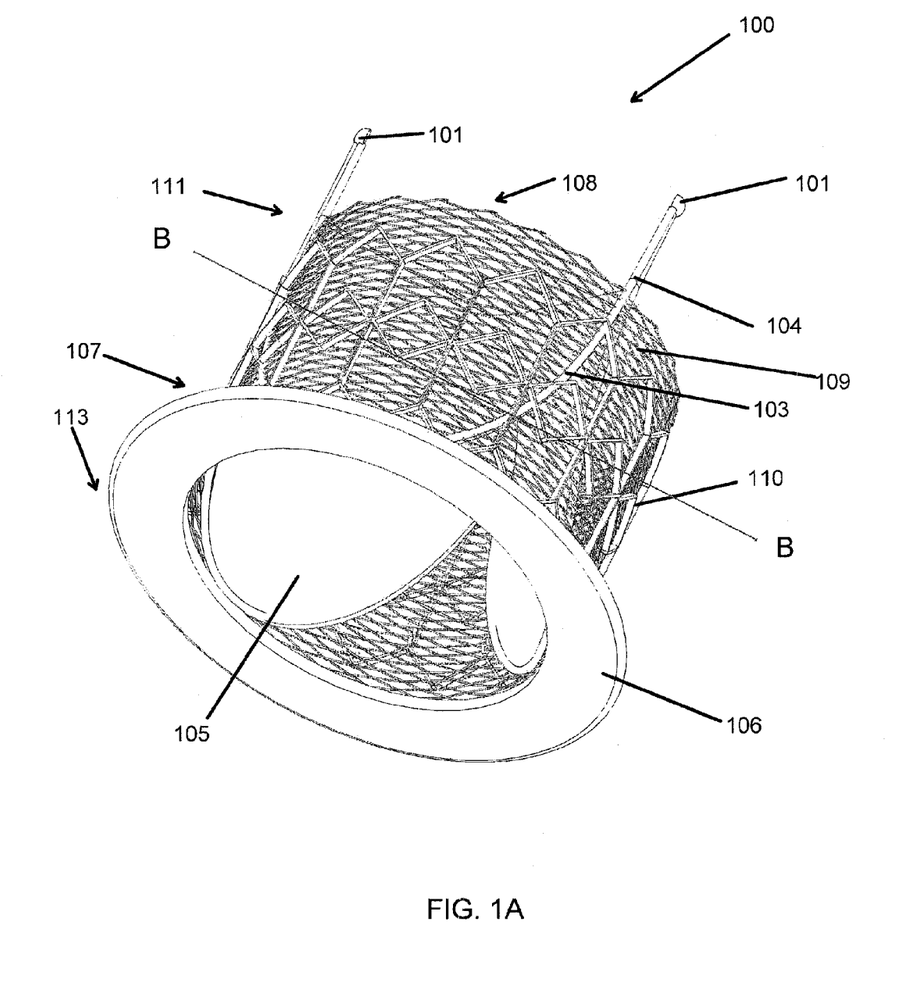
FIG. 1A illustrates a perspective view of a fully expanded stent-valve system, according to some embodiments of the invention.

FIG. 1A illustrates a perspective view of a fully expanded valve replacement 100, according to some embodiments of the invention. The valve 100 includes an outer scaffold stent 110, and an inner valve support 109 having relatively upstream (e.g., distal) end 107 and relatively downstream (e.g., proximal) end 108. For clarity, upstream or distal to, for example, the aortic valve annulus shall refer to herein a direction toward the left ventricle. Downstream, or proximal to, for example, the aortic valve annulus shall refer to herein a direction toward the aorta.

The scaffold stent 110 can have an inner surface and an outer surface, the outer surface configured to exert a radially outward force and engage with, for example, the native valve annulus when the scaffold stent 110 is in an expanded configuration. The valve support 109 can engage with the scaffold stent 110 via a radial outward mechanical force, and/or anchors such as hooks for example, as described in greater detail below. In some embodiments, the scaffold stent 110 can have an inner, or an outer diameter of between about 20 mm and about 30 mm, or between about 23 mm and about 29 mm.

Still referring to FIG. 1A, the valve support 109 has a reduced configuration for delivery and an expanded configuration, and may have a frame, e.g., a stent. In some embodiments, the valve support includes a hollow self-expandable structure that has at least a portion substantially shaped, for example, like a cylinder or another appropriate shape. In some embodiments, the valve support 109 includes a nitinol mesh cylinder that has an axial length of between about 1 cm and about 4 cm, or between 2 cm and about 3 cm. The valve support 109 can have a diameter in its expanded configuration sufficient to be housed within, and attach to the scaffold stent 110 as shown, such as by radial force and/or additional anchors on the valve support 109 and/or the scaffold stent 110. The valve support 109 has an upstream end 113 and a downstream end 111. The upstream, or distal end 113 of the valve support can include an integrally formed or otherwise connected portion that extends radially outwardly, such as a flap 106 (also referred to as a flange or ring 106). In some embodiments, the flap 106 resembles the outer portion of an interatrial septal disk occluder. The flap 106 can have, in some embodiments, an inner diameter configured to allow the passage of blood therethrough, and an outer diameter that is greater than the inner diameter of the scaffold stent 110. In some embodiments, the flap 106 is configured to prevent embolization of the valve 100 downstream, e.g., toward the aorta (for an aortic valve replacement). In some embodiments, the flap 106 can be made of the same or a different material than the rest of the valve support 109, e.g., a shape memory material. The flap 106 in some embodiments can be expandable. The flap 106 can be made, for example, of a mesh structure. The mesh structure could have a plurality of layers, such as a double-layer mesh. The mesh structure can be filled with an appropriate material such as, for example PTFE, a polyester patch, or other fabric in order to prevent or minimize paravalvular aortic regurgitation, e.g., regurgitation of blood from the aorta towards the left ventricle around the scaffold stent 110.

The valve support 109 can also include a valve skirt (not shown) that is operably attached, by sutures, adhesives, or other means, to the inner or outer surface of the valve support. The valve skirt can be made of any appropriate material, such as a metal, a synthetic polymer such as PET, Dacron, ePTFE, or PTFE for example, and/or a biological material such as pericardium, pleura, peritoneum, small intestinal submucosa, collagen, or the like. The valve skirt can assist in reducing paravalvular leak and associated regurgitation around the valve. Operably coupled to the valve support 109, e.g., via the valve skirt are the valve leaflets 105. Each valve could include any number of leaflets, such as 2, 3, or 4 leaflets for example. The leaflets 105 can also be made of any appropriate material including materials described above in connection with the valve skirt. In some embodiments, the lateral ends of the leaflets 105 include enlarged regions that are folded to both form commissural joints and fasten the commissural joints to the valve support 109. The skirt and leaflets 105 can, in some embodiments, be configured so that the joints align with contours of the cell pattern of the valve support 109.

Still referring to FIG. 1A, the valve support 109 can also include a plurality of struts or posts 104. When the valve is in use, the struts 104 can be oriented generally parallel to the longitudinal axis of the valve support 109. While three struts 104 are shown, any number of struts 104, such as two or four struts for example could also be present. The struts 104 can be made up of a plurality of separate elongate members 103 as shown that operably connect at upstream ends 103, or in other embodiments be made of a single elongate member. As will be illustrated later, the struts 104 can be flexible and all struts 104 can bend, e.g., radially inwardly in order to compress the valve leaflets 105 together and reduce the delivery profile of the valve 100. The struts 104 can be releasably connectable in a reduced delivery configuration, such as at a point along the longitudinal axis of the valve 100. In some embodiments, the struts 104 can have an axial length that is greater, such as at least 10%, 20%, 30%, 40%, 50%, or more greater than the axial length of the valve support 109 and/or the scaffold stent 110. Disposed on the distal end of each of the struts 104 are retaining structures 101 with an enlarged surface area compared to the remainder of the body of the struts 104. The retaining structures 101 can collectively form a spherical configuration when connected together, although other shapes, e.g., a cube, pyramid, etc. are also possible. Each of the plurality of retaining structures 101 can be releasably held together by, for example, a snare, movable jaws, or a bioptome-like member, as illustrated elsewhere herein. In other embodiments, the retaining structures 101 can be releasably held together via a suture that can be ligated or untied during delivery. Other releasable detachment mechanisms between the retaining structures 101 and a delivery cable within a lumen of the delivery catheter including electrolytic detachment, an adhesive, and the like are also possible. In some embodiments, the tool to releasably hold the retaining structures 101 together can be as described, for example, in U.S. Pub. No. 2012/0143301 to Maslanka et al., which is hereby incorporated by reference in its entirety.

Figure 1B:
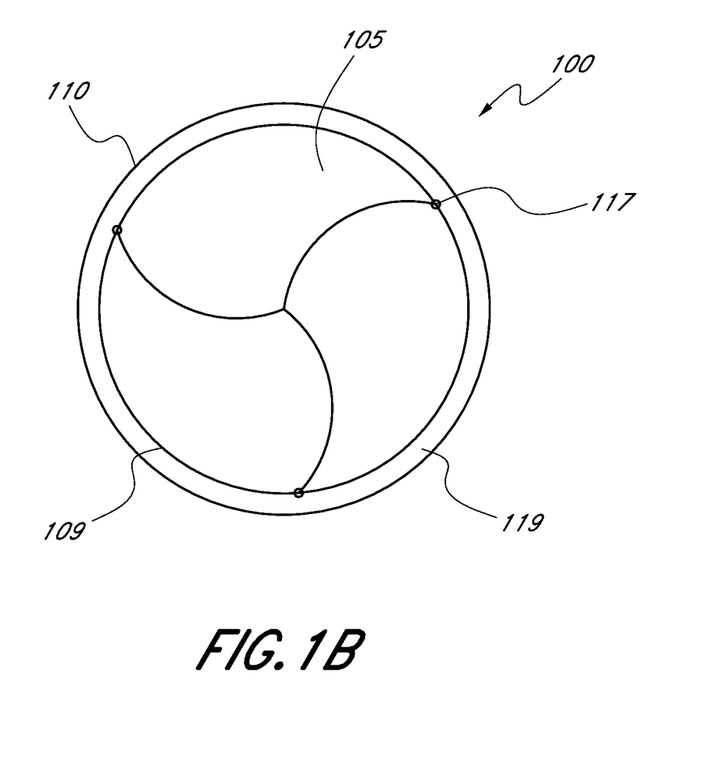
FIG. 1B is a schematic cross-sectional view of the valve through line B-B of FIG. 1A.

FIG. 1B is a schematic cross-sectional view of the valve 100 through line B-B of FIG. 1A. Shown is the scaffold stent 110, and valve support 109 can comprise a shape memory material such as nitinol (e.g., nitinol mesh) or a shape memory polymer to allow for self-expansion. Alternatively the frame of the valve support 109 can be made of another metal or metal alloy. In some embodiments, the valve support 109 frame is made of a single layer, or a plurality of layers. The valve skirt (not shown) can reside, for example, in between the scaffold stent 110 and valve support 109 in space 119, and attached, such as sewn to, for example, the scaffold stent 110. In some embodiments, the valve skirt can be attached to the outer surface of the scaffold stent 110. Also shown are leaflets 105 which can be attached to the valve support 109, such as via suture for example, at joints 117.

Figure 2:
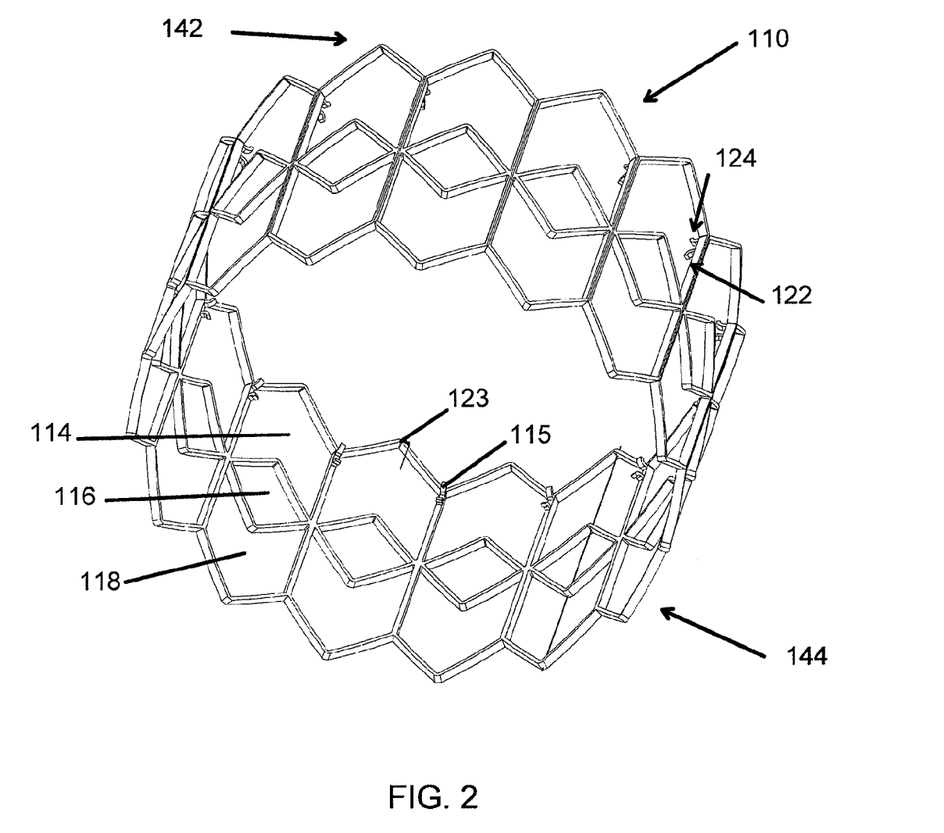
FIG. 2 illustrates an embodiment of a scaffold stent, as part of a valve replacement system.

As illustrated in FIG. 2, the scaffold stent 110 has a proximal end 142 and a distal end 144, and a plurality of rows of cells 114, 116, 118 therebetween. The stent 110 can have any appropriate wall or cell pattern depending on the desired clinical result, with vertex peaks 123 and valleys 115 as illustrated for example. In some embodiments as shown, the proximal and distal rows of cells 114, 118 respectively are larger in area than the central row of cells 116, although other cell patterns having equal or unequal areas, and numbers of rows of cells are also possible.

Still referring to FIG. 2, the distal end 144 or the proximal end 142 of the stent 110 can include one, two, three, or more rows of anchors such as hooks 122, 124. In some embodiments, the rows of hooks 122, 124 are spaced circumferentially apart, such as about 2-3 mm symmetrically or substantially symmetrically circumferentially apart from each other when the stent 110 is in an expanded configuration. In some embodiments, the hooks 122, 124 can be staggered axially as opposed to being in discrete rows. The hooks 122, 124 can be configured to face radially inwardly as illustrated in order to retain the self-expanding independent structure (e.g., the stent-valve) upon which the valve leaflets are attached. In some embodiments, each row of hooks 122, 124 can have the hook portion be directed upstream (e.g., toward the aorta for an aortic valve) in order to prevent embolization toward the ventricle through diastolic pressure. In some embodiments, each row of hooks can have the hook portion directed downstream (e.g., toward the left ventricle for an aortic valve), or a first row (e.g., a proximal or distal row of hooks) facing upstream, while a second row (the other of the proximal or distal row of hooks) faces downstream, as illustrated in FIG. 2. In some embodiments, each axially spaced-apart row of hooks includes a plurality of hooks, such as between 2-12 hooks, such as 2, 4, 6, 8, 10, or 12 hooks for example. The scaffold stent 110 can be made of any appropriate material, such as a metal or metal alloy, including stainless steel, Nitinol, or Elgiloy, or a polymer, for example. The scaffold stent 110 can be either self-expandable or balloon-expandable. In some embodiments, the scaffold stent 110 can be operably complexed to a therapeutic agent, such as a drug for example, via various eluting techniques. The scaffold stent 110 can be generally cylindrical as shown, or take another shape, such as an hourglass for example, depending on the anatomy and desired clinical result.

Figures 3A, 3B:
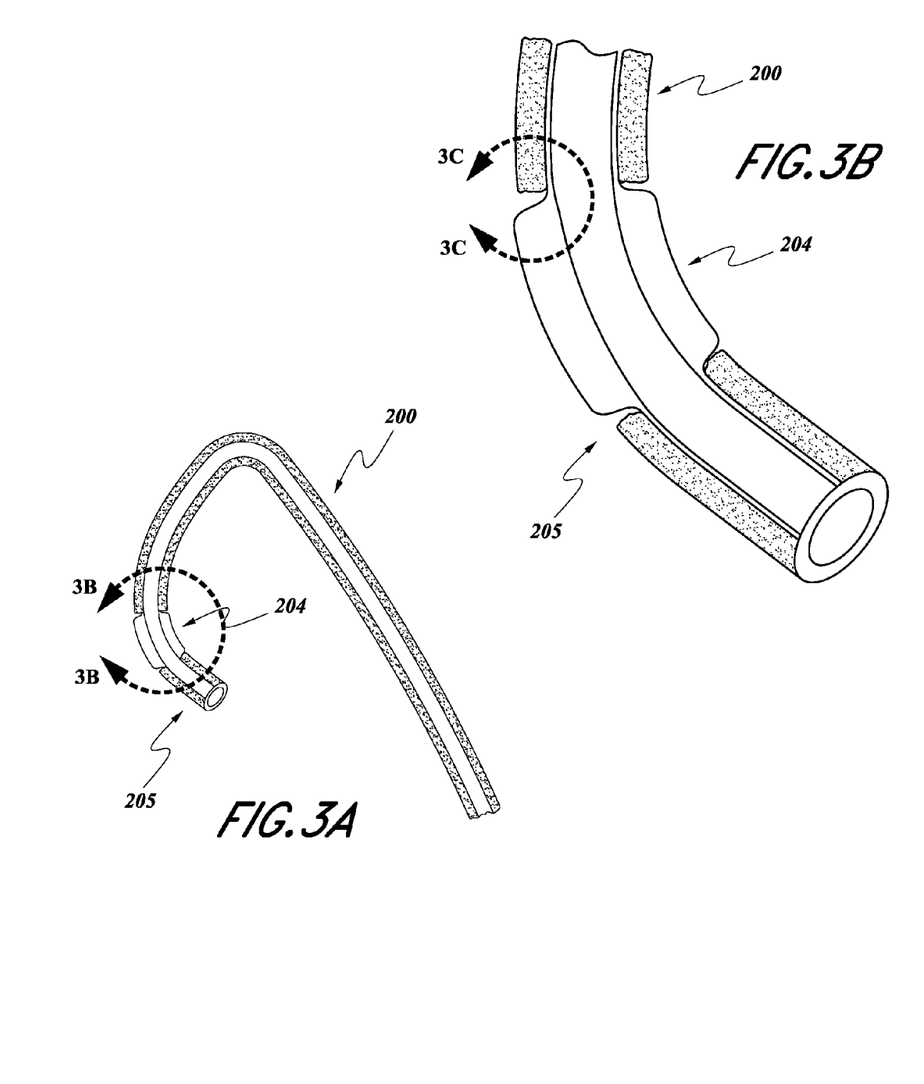
FIG. 3A schematically illustrates a delivery catheter with an expandable member, such as a balloon on its distal end, configured to radially expand the scaffold stent, according to some embodiments of the invention.
FIG. 3B illustrates a close-up view of the distal end of the delivery catheter of FIG. 3A, showing a balloon.
Figure 3C:
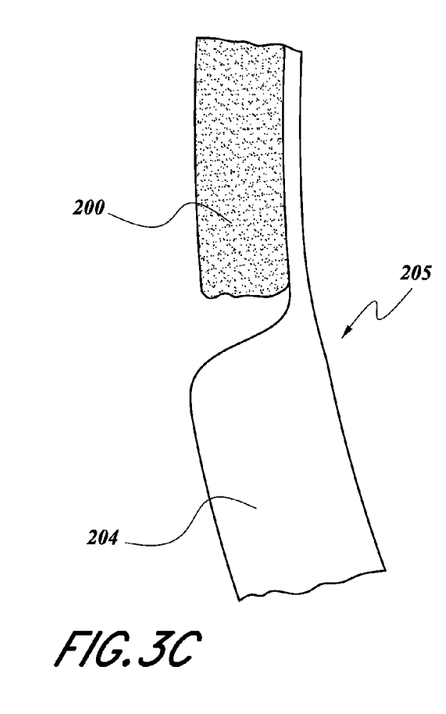
FIG. 3C schematically illustrates an extrusion detail of the distal end of the delivery catheter shown in FIGS. 3A-3B.

FIG. 3A schematically illustrates a delivery catheter 200 with an expandable member, such as a balloon 204 on its distal end 205, configured to radially expand the scaffold stent 110. FIG. 3B illustrates a close-up view of the distal end 205 of the delivery catheter 200, showing balloon 204. In some embodiments, the balloon can have an axial length of between about 15 mm-30 mm, such as about 20 mm, and an inflated diameter of between about 20 mm-35 mm, such as between about 20 mm and about 30 mm. FIG. 3C schematically illustrates an extrusion detail of the distal end 205 of the delivery catheter 200, showing wall of balloon 204 co-extruded to the wall of the delivery catheter 200. In some embodiments, the balloon can be formed by blow-molding or other techniques.

Figure 4:
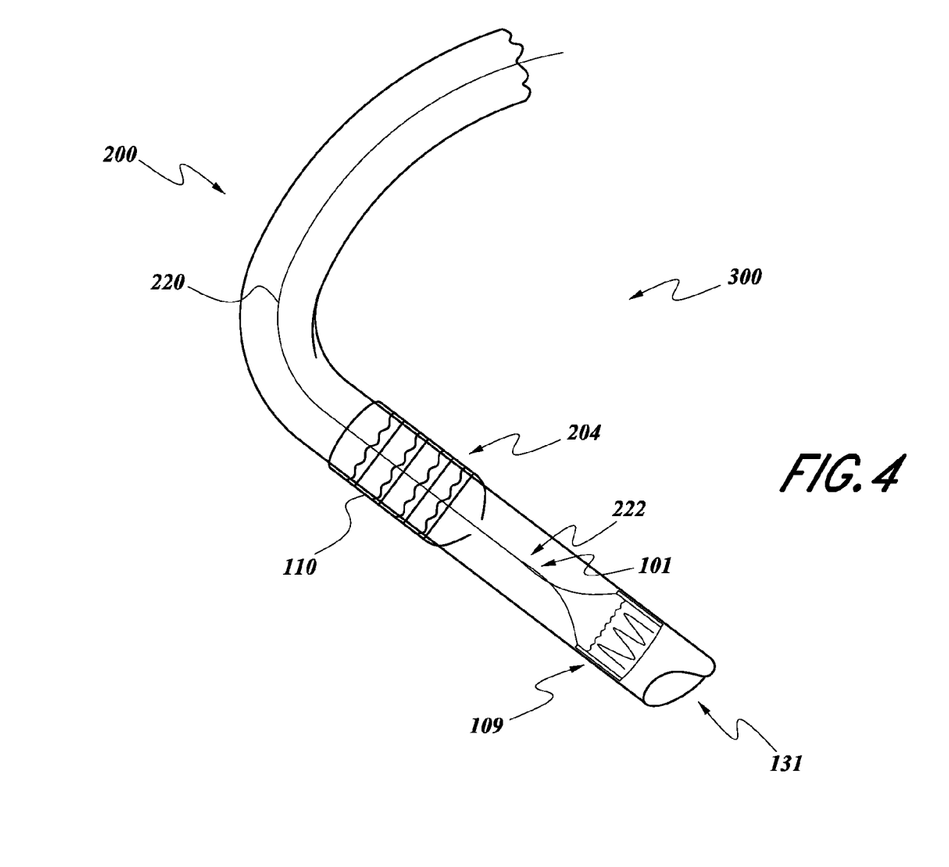
FIG. 4 schematically illustrates a delivery system including delivery catheter, scaffolding stent, and transcatheter heart valve.

FIG. 4 schematically illustrates a delivery system 300 including delivery catheter 200. Disposed over the balloon 204 and the delivery catheter 200 is the scaffold stent 110 in a reduced configuration. Housed within a lumen 131 of the delivery catheter 200 is the valve support 109. The valve support 109 is axially movable within the delivery catheter 200 lumen by virtue of its connection to the delivery cable 220 via bioptome 222 or other releasable connection connected to apex point 101 as described elsewhere herein.

In other embodiments, the scaffold stent 110 is self-expandable, and made of a shape memory material such as nitinol as described elsewhere herein. The scaffold stent 110 can be mounted over a distal portion of the delivery catheter 300 as described above, which can be 8-12 French or less in some cases. The scaffold stent 110 may have a slightly flared distal end in some embodiments, and in some cases be covered on its inner and/or outer surface by a fabric such as PTFE. The stent 110 can be covered by a restraint feature such as a retractable sheath having sufficient column strength to prevent the stent 110 from transforming from the reduced configuration to the expanded configuration while undeployed. The stent 110 can be resheathable prior to delivery, to permit repositioning if necessary. Once the stent 110 is positioned over the native valve annulus, the sheath can be retracted or otherwise removed, allowing the stent 110 to fully self-expand and be positioned at the level of the native valve annulus.

Figure 5:
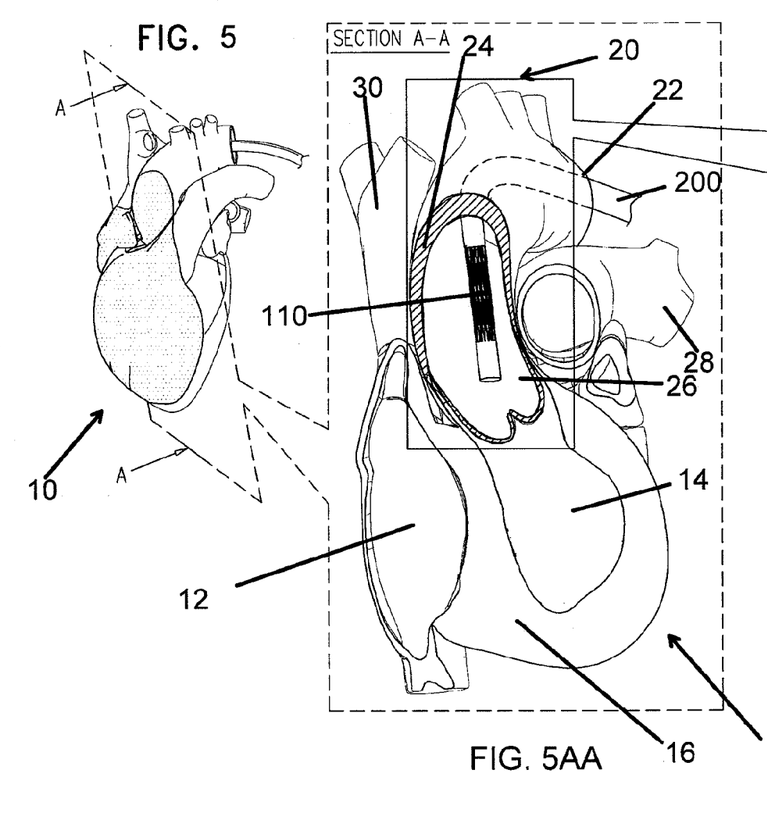
FIGS. 5 and 5A-5G illustrate a system and multiple-stage method for delivering a transcatheter heart valve, according to some embodiments of the invention.
Figure 5A:
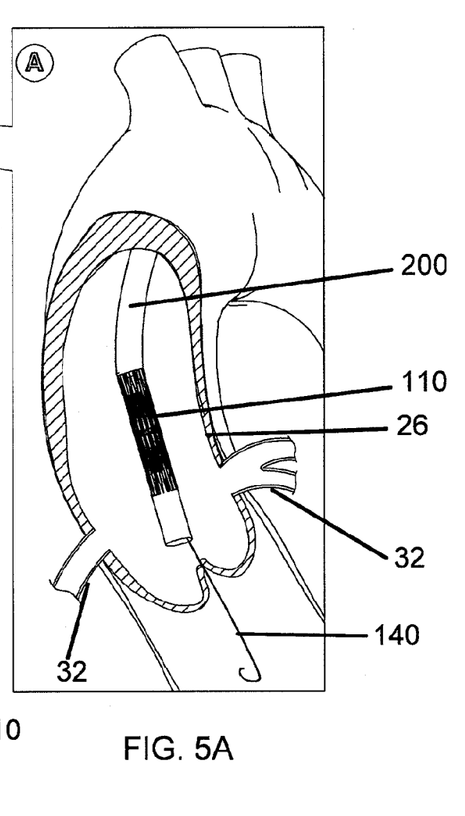
Figure 5B:
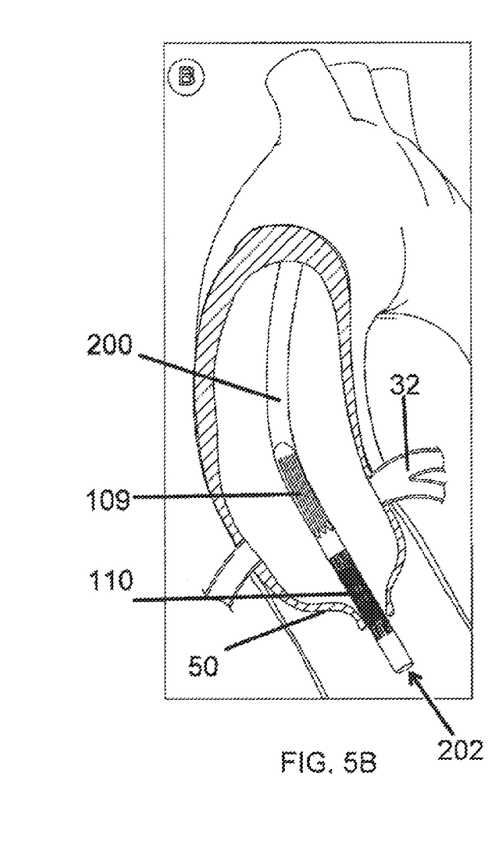
Figure 5C:
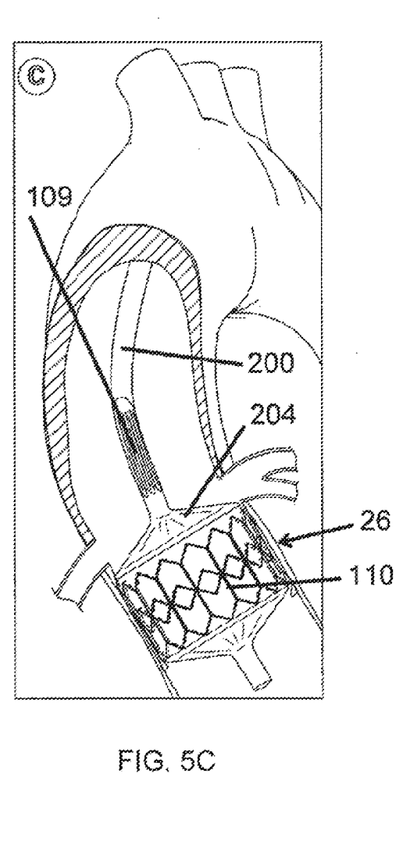
Figure 5D:
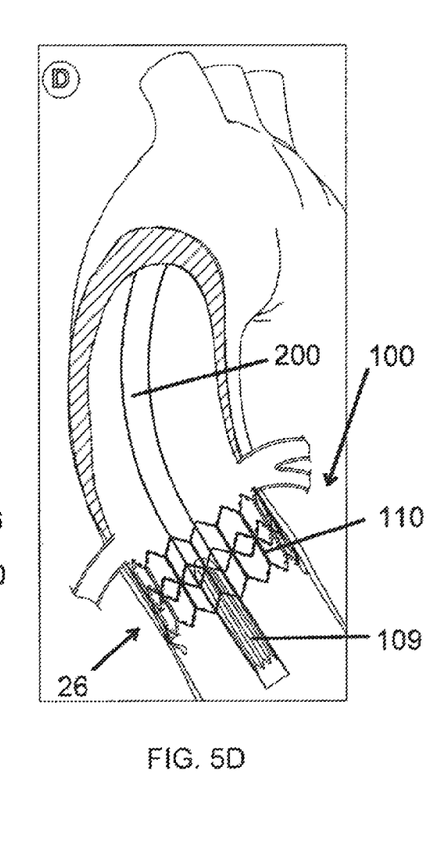
Figure 5E:
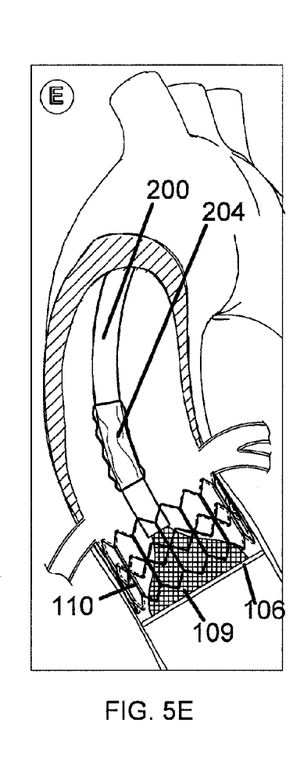
Figure 5F:
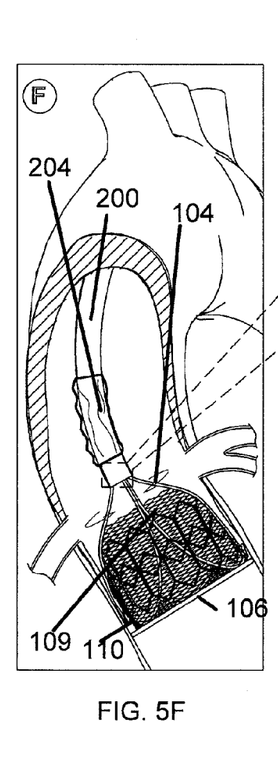
Figure 5G:
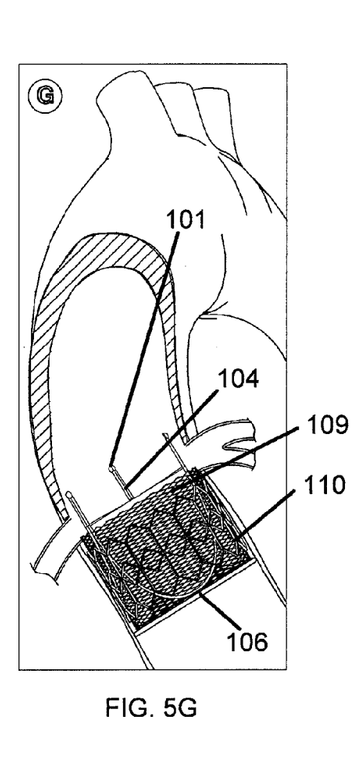

FIGS. 5-5G illustrate a system and multiple-stage method for delivering a transcatheter heart valve, according to some embodiments of the invention. As noted, the system and method can be adapted for use for mitral, tricuspid, or pulmonic valve replacement, for example; the aforementioned figures illustrate an aortic valve replacement as one example. FIG. 5 illustrates a perspective view of a heart and the great vessels. As shown in FIG. 5AA, which is a call-out cross-section through the heart (line A-A of FIG. 5) are the heart 10 and great vessels, showing various anatomy including the aortic valve annulus 26, ascending aorta 24, aortic arch 20, superior vena cava 30, pulmonary artery 28, right ventricle 12, left ventricle 14, and interventricular septum 16. Also shown is the scaffold stent 110 disposed over the delivery catheter 200. As shown in FIG. 5A, the delivery catheter 200 is introduced, such as retrograde, from an access point, such as the femoral or brachial artery, for example, upstream into the aorta, aortic arch 20, ascending aorta 24, and into the native aortic valve annulus 26, proximate the coronary arteries 32. In some embodiments, the valve 100 is configured such that it does not disrupt blood flow into coronary arteries 32 when deployed, and also does not obstruct subsequent catheter access to the coronary arteries 32.

The delivery catheter 200 can be introduced over a guidewire 140 as shown. As illustrated in FIG. 5B, the premounted balloon-expandable scaffold stent 110 is then carried by the delivery catheter 200 and positioned at the level of the native valve annulus 26. The scaffold stent 110 is mounted over a distal portion 202 of the delivery catheter 200, while the valve support 109 is housed within a lumen of the delivery catheter 200. In some embodiments, the scaffold stent 110 can have a flared distal end. In some embodiments, the delivery catheter 200 can be between 8-12 or 8-10 French in size, or less than 12, 11, 10, 9, 8, 7, 6, or less French.

As illustrated in FIG. 5C, once proper position over the aortic valve annulus 26 is achieved, the scaffold stent 110 can then be radially expanded via one or more expandable members, such as a balloon 204 on the delivery catheter 200, and the native valve leaflets 50 are then secured against the sidewall of the annulus 26. In other embodiments, the scaffold stent 110 is self-expandable rather than balloon-expandable, and in some embodiments can be carried within a lumen of the delivery catheter 200 rather than mounted over the delivery catheter 200, or mounted near the distal end of the delivery catheter 200 and covered by a retractable sheath prior to delivery. The valve support 109 can remain within the lumen of the delivery catheter and await separate delivery.

Next, as illustrated in FIG. 5D, the remainder of the valve 100 including valve support 109 is then delivered separately through the delivery catheter 200 such that the distal end of the delivery catheter 200 remains upstream of the scaffold stent 110. FIG. 5E illustrates the valve support 109 being partially deployed, for example, by downstream retraction of the delivery catheter 200 relative to the valve support 109 or by upstream advance of a delivery cable releasably connected to the valve support 109. The balloon 204 has returned to its deflated state as shown. The distal flap 106 of the valve support 109 is first exposed beyond the distal end of the delivery catheter 200. The catheter 200 and the exposed flap 106 are then retracted as a unit until the flap 106 engages the distal end of the scaffold stent 110 as shown in FIG. 5F. At this point in time, despite not being fully expanded, the leaflets attached to the valve support 109 can be already functional. As shown, the upstream ends of the plurality of struts remain bowed and connected at an apex point via a grasping member, e.g., a bioptome. By further retraction of the delivery catheter 200 the valve support 109 fully transforms from the reduced configuration to the fully expanded configuration, engaging the hooks 122, 124 of the scaffold stent 110. As shown in FIG. 5G, the bioptome is released and the delivery cable retracted, allowing the upstream retaining ends of the struts 104 to expand radially outwardly, allowing the prosthetic valve's leaflets to also expand and be fully functional. In other embodiments, the valve can be delivered through a trans-aortic thorascopic, or open approach as known in the art. As shown in the call-outs of FIG. 5FF, the retaining end structures 101 of the struts 104 transform from a reduced configuration forming a spherical structure 101' when held in place by the bioptome 222 to an enlarged configuration following a release of the bioptome 222, where the spherical structure 101' separates into a plurality of individual retaining end components 101.

Figure 6:
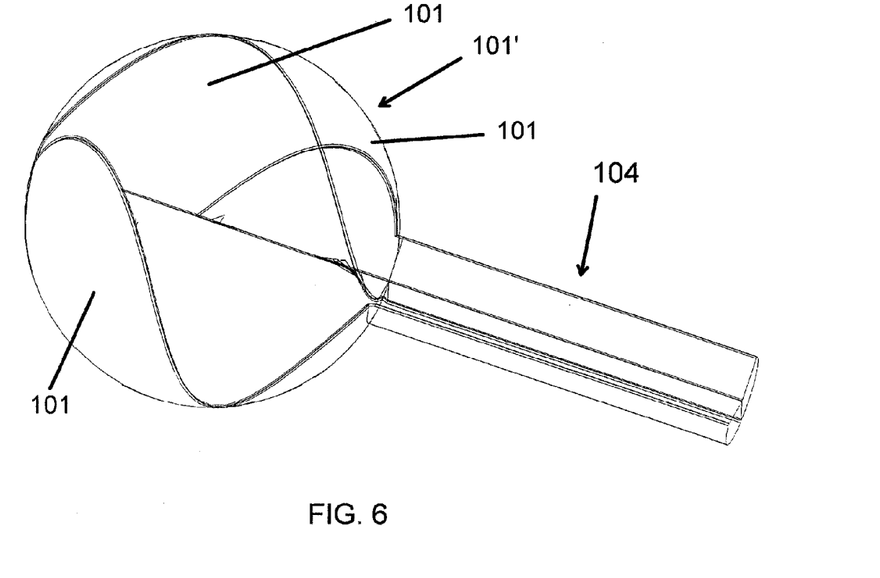
FIG. 6 illustrates a plurality of retaining structures forming ends of strut members of a valve support, coupled together to form a sphere-like shape, according to some embodiments of the invention.

FIG. 6 illustrates a plurality (e.g., 3 as shown) of retaining end structures 101 as described elsewhere herein, and coupled together to form a spherical structure 101' akin to a ball formed by a plurality of puzzle-like pieces configured to fit together, such as when held together by a tool, such as a grasping member 222.

Figure 6A:
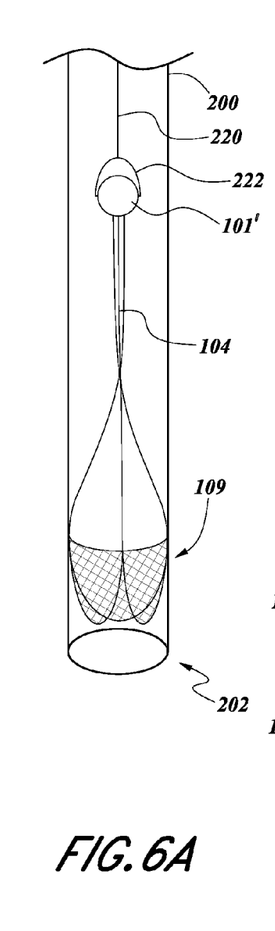
FIGS. 6A-6E illustrate in more detail the delivery sequence for the valve support illustrated in FIGS. 5D-5G above.
Figure 6B:
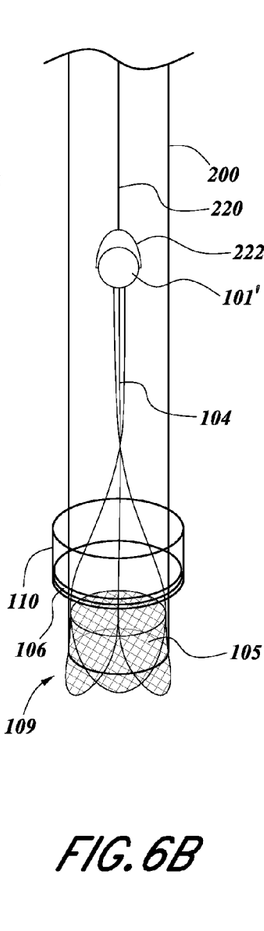
Figure 6C:
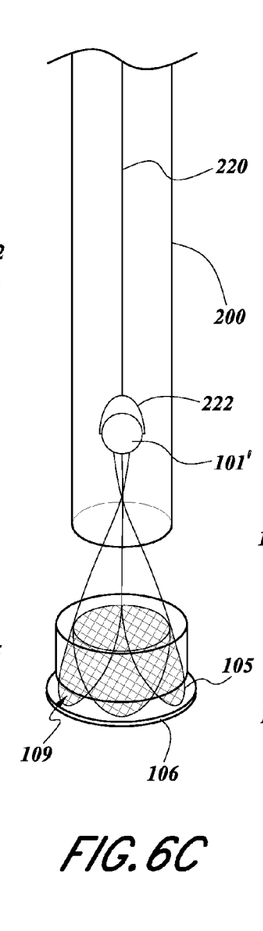
Figures 6D, 6E:
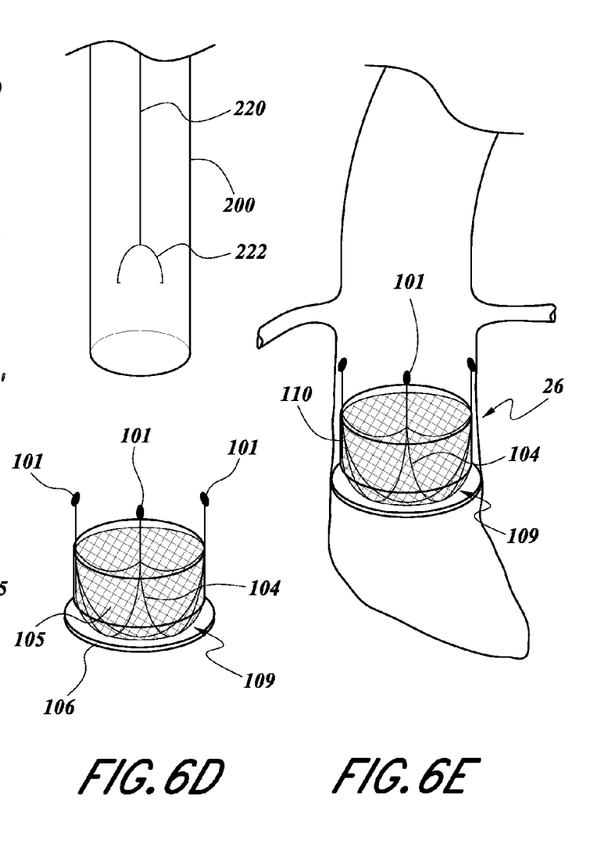

FIGS. 6A-6E illustrate in more detail the delivery sequence for the valve support illustrated in FIGS. 5D-5G above. FIG. 6A schematically illustrates the valve support 109 in a reduced configuration within the delivery catheter, with retaining end structures 101 of the struts 104 collapsed together at apex point (e.g., sphere 101'). While the apex point could be shaped as a sphere as illustrated, ovoid, pyramidal, cubical, and other configurations are also possible. A bioptome 222, snare, movable jaws, or the like is releasably connected to the apex point 101'. The bioptome 222 is in turn operably connected to delivery cable 220. FIG. 6B illustrates valve support 109 and associated components moving distally out of the delivery catheter 200 and self-expanding. FIG. 6C illustrates the valve support 109 fully removed from the delivery catheter, with bioptome 222 still attached to the sphere 101' As illustrated in FIG. 6D, the bioptome 222 releases from the sphere 101', and each of the struts 104 move radially apart from each other, due to their natural bias for example, separating the post and sphere 101' into, for example, fractions of three (individual struts 104 with their associated retaining end structure 101). This causes the valve leaflets 105 to unfold. FIG. 6E shows the fully-expanded and deployed valve 100 with the valve support 109 at least partially within the scaffold stent 110 as previously described.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "positioning the distal end of the delivery catheter in the native aortic valve annulus" include "instructing the positioning of the distal end of the delivery catheter in the native aortic valve annulus." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of within less than 1% of, within less than 0.1% of, and within less than 0.01% of the stated amount

What is claimed is:

1. A heart valve replacement system, comprising:
a delivery catheter having a proximal end, a central lumen, and a distal end;
a scaffold stent configured to fit over a portion of the delivery catheter proximate the distal end of the delivery catheter, the scaffold stent having a reduced delivery configuration and an expanded configuration;
a valve support comprising a frame and a plurality of leaflets attached to the frame, the frame comprising a downstream end, an upstream end, and a plurality of struts extending axially from the frame, each strut having a retaining structure at the downstream end, the valve support having a reduced delivery configuration wherein the valve support is housed within the central lumen of the delivery catheter, wherein the valve support is located distal of the scaffold stent, and wherein the valve support is configured to be delivered independent of the scaffold stent; and
a grasping member configured to operably attach to the retaining structures of the plurality of struts to compress the valve leaflets, and wherein the retaining structures couple together to form a spherical shape.

2. The heart valve replacement system of claim 1, further comprising an expandable member proximate the distal end of the delivery catheter, the expandable member configured to expand the scaffold stent.

3. The heart valve replacement system of claim 1, wherein the expandable member comprises a balloon.

4. The heart valve replacement system of claim 1, wherein the scaffold stent is self-expandable, and wherein a retaining mechanism is configured to maintain the scaffold stent in a reduced configuration during delivery.

5. The heart valve replacement system of claim 1, wherein the delivery catheter has a size of less than or equal to 12 French.

6. The heart valve replacement system of claim 1, wherein the delivery catheter has a size of between 8 French and 12 French.

7. The heart valve replacement system of claim 1, wherein the grasping member comprises a bioptome.

8. The heart valve replacement system of claim 1, wherein the grasping member comprises a snare.

9. The heart valve replacement system of claim 1, wherein the frame of the valve support comprises a shape memory mesh material.

10. The heart valve replacement system of claim 1, comprising a valve skirt attached to a surface of the scaffold stent.

11. The heart valve replacement system of claim 10, wherein the valve skirt comprises a fabric material.

12. The heart valve replacement system of claim 10, wherein the frame of the valve support comprises a generally cylindrical portion, and a flap portion on an upstream end of the frame configured to rest against an upstream end of the scaffold stent, the flap portion configured to minimize or prevent paravalvular regurgitation.

13. The heart valve replacement system of claim 1, wherein the plurality of struts comprises at least 3 struts.

14. The heart valve replacement system of claim 1, configured to replace a native aortic valve.

15. A transluminal method of delivering an aortic valve replacement, comprising the steps of:
providing a delivery catheter carrying a scaffold stent over a distal portion of the delivery catheter, the scaffold stent having an upstream end and a downstream end, the delivery catheter also comprising a central lumen and a valve support having a frame, a plurality of valve leaflets, and a distal flap portion, the valve support further having a plurality of struts extending axially from the frame, each strut having a retaining structure at the downstream end, wherein the retaining structures couple together to form a spherical shape, wherein the retaining structures are releasably connected to a delivery cable, the valve support not connected to the scaffold stent, and wherein the valve support is positioned inside the lumen of the delivery catheter and distal of the scaffold stent;
positioning the distal end of the delivery catheter in the left ventricle, to position the scaffold stent at the level of the native aortic valve annulus;
expanding the scaffold stent within the native aortic valve annulus;
partially moving the valve support out of the delivery catheter, thereby expanding the distal flap portion;
retracting the valve support such that the distal flap contacts the downstream end of the scaffold stent;
disconnecting the valve support from the delivery cable; and
withdrawing the delivery catheter and the delivery cable.

16. The method of claim 15, wherein disconnecting the valve support from the delivery cable comprises releasing a grasping member connected to the retaining structures on distal ends of the plurality of struts, whereby releasing of the grasping member causes the valve leaflets to completely unfold.

17. The method of claim 16, wherein the grasping member comprises a bioptome.

18. The method of claim 15, further comprising the step of securing the valve support to the scaffold stent.

19. The method of claim 18, wherein securing the valve support to the scaffold stent comprises connecting the frame of the valve support to a plurality of hooks on a radial inwardly-facing surface of the scaffold stent.

20. The method of claim 15, wherein expanding the scaffold stent within the native aortic valve annulus comprises balloon-expanding the scaffold stent.

21. The method of claim 15, wherein expanding the scaffold stent within the native aortic valve annulus comprises allowing the scaffold stent to self-expand.

* * * * *